(12) United States Patent
Han et al.

(10) Patent No.: US 12,109,067 B2
(45) Date of Patent: Oct. 8, 2024

(54) POSITIONING ARM APPARATUS FOR ULTRASOUND HEAD

(71) Applicant: IMGT CO., LTD., Seongnam-si (KR)

(72) Inventors: Kyu Hoon Han, Seongnam-si (KR); Young Bok Yu, Seoul (KR); Keon Ho Son, Seongnam-si (KR)

(73) Assignee: IMGT CO., LTD., Seongnam-si (KR)

( * ) Notice: Subject to any disclaimer, the term of this patent is extended or adjusted under 35 U.S.C. 154(b) by 0 days.

(21) Appl. No.: 18/358,359

(22) Filed: Jul. 25, 2023

(65) Prior Publication Data

US 2024/0252144 A1  Aug. 1, 2024

(30) Foreign Application Priority Data

Jan. 27, 2023 (KR) .......................... 10-2023-0011192

(51) Int. Cl.
| | | |
|---|---|---|
| *A61N 7/02* | (2006.01) | |
| *A61B 8/00* | (2006.01) | |
| *F16M 11/04* | (2006.01) | |
| *F16M 11/20* | (2006.01) | |
| *F16M 13/02* | (2006.01) | |

(52) U.S. Cl.
CPC .............. *A61B 8/4218* (2013.01); *A61N 7/02* (2013.01); *F16M 11/04* (2013.01); *F16M 11/2064* (2013.01); *F16M 13/022* (2013.01); *F16M 2200/022* (2013.01); *F16M 2200/068* (2013.01)

(58) Field of Classification Search
CPC ...... A61N 7/02; A61B 8/4218; F16M 13/022; F16M 11/2064; F16M 11/04
USPC .......................................... 248/674; 600/439
See application file for complete search history.

(56) References Cited

U.S. PATENT DOCUMENTS

| | | | |
|---|---|---|---|
| 5,779,209 A | 7/1998 | Rello | |
| 7,925,330 B2* | 4/2011 | Kalafut | A61M 5/14546 |
| | | | 600/431 |
| 7,993,289 B2* | 8/2011 | Quistgaard | A61B 34/32 |
| | | | 601/3 |
| 9,238,099 B2* | 1/2016 | Kalafut | G16H 40/63 |
| 9,950,107 B2* | 4/2018 | Kalafut | A61M 5/14546 |

(Continued)

FOREIGN PATENT DOCUMENTS

| | | |
|---|---|---|
| JP | 2012-005646 A | 1/2012 |
| JP | 2015-0077418 A | 4/2015 |

(Continued)

OTHER PUBLICATIONS

Japanese Office Action issued on Mar. 19, 2024, in counterpart Japanese Patent Application No. 2023-122496 (5 pages in English).
Office Action Issued Mar. 7, 2023 in counterpart Korean Patent Application KR 10-2023-0011192 (4 Pages in Korean).
Notice of Allowance Issued Jun. 16, 2023 in Counterpart Korean Patent Application KR 10-2023-0011192 (3 Pages in Korean).

(Continued)

*Primary Examiner* — Todd M Epps
(74) *Attorney, Agent, or Firm* — NSIP Law

(57) ABSTRACT

A positioning arm apparatus for an ultrasound head is provided. The positioning arm apparatus for an ultrasound head according to an embodiment may constantly move the ultrasound head without change in height of the ultrasound head according to a moving distance by simultaneous rotation at two positions and tilting motion at one position. Also, the positioning arm apparatus may be miniaturized and lightweight since it is operated with a mechanical mechanism, and may provide strong fixing strong and easy maneuverability.

5 Claims, 5 Drawing Sheets

(56) References Cited

U.S. PATENT DOCUMENTS

| | | | |
|---|---|---|---|
| 10,166,326 | B2 | 1/2019 | Kalafut et al. |
| 2005/0154431 | A1 | 7/2005 | Quistgaard et al. |
| 2007/0213662 | A1 | 9/2007 | Kalafut et al. |
| 2007/0282263 | A1 | 12/2007 | Kalafut et al. |
| 2010/0204578 | A1 | 8/2010 | Schmidt et al. |
| 2012/0016233 | A1 | 1/2012 | Kalafut et al. |
| 2014/0314538 | A1 | 10/2014 | Carter et al. |
| 2015/0182687 | A1 | 7/2015 | Kalafut et al. |
| 2016/0100822 | A1* | 4/2016 | Kim .................. A61B 8/14 600/472 |
| 2019/0365347 | A1* | 12/2019 | Abe ................ A61B 5/0095 |
| 2022/0152426 | A1 | 5/2022 | Cho et al. |

FOREIGN PATENT DOCUMENTS

| | | | |
|---|---|---|---|
| JP | 2020-519327 | A | 7/2020 |
| KR | 10-2006-0113930 | A | 11/2006 |
| KR | 10-2010-0121277 | A | 11/2010 |
| KR | 10-2022-0097177 | A | 7/2022 |

OTHER PUBLICATIONS

Korean Office Action issued on Mar. 7, 2023 in corresponding Korean Patent Application No. 10-2023-0011192. (4 pages in Korean and 5 pages in English).

Korean Decision to Grant a Patent issued on Jun. 16, 2023 in corresponding Korean Patent Application No. 10-2023-0011192. (2 pages in Korean and 2 pages in English).

Extended European search report issued on Jul. 11, 2024, in counterpart European Patent Application No. 23186554.4 (8 pages).

* cited by examiner

POSITIONING ARM APPARATUS FOR ULTRASOUND HEAD

CROSS-REFERENCE TO RELATED APPLICATION(S)

This application claims the benefit under 35 USC § 119(a) of Korean Patent Application No. 10-2023-0011192, filed on Jan. 27, 2023, in the Korean Intellectual Property Office, the entire disclosure of which is incorporated herein by reference for all purposes.

BACKGROUND

1. Field

The following description relates to diagnosis and treatment technology using ultrasound, and more particularly, to image scanning and treatment technology using focused ultrasound (FUS) for image guide therapy.

2. Description of Related Art

Ultrasound signals may be used in the treatment of biological tissues, such as cancer, tumors, lesions, and the like. Treatment with ultrasound is a method of treating a lesion by emitting ultrasound signals to the lesion of the human body. Ultrasound treatment may cause less trauma of a patient, compared to general surgical treatment or chemotherapy, and realize non-invasive treatment. Examples of the application of ultrasound treatment include liver cancer, bone sarcoma, breast cancer, pancreatic cancer, kidney cancer, soft tissue tumors, pelvic tumors, and the like.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an embodiment, a positioning arm apparatus for an ultrasound head which can constantly move the ultrasound head without change in height of the ultrasound head according to a moving distance, can be miniaturized and lightweight, and provides strong fixing force and easy maneuverability is proposed.

In one general aspect, there is provided a positioning arm apparatus for an ultrasound head, the positioning arm apparatus comprising a first link provided with a first joint at a lower end of one side thereof and a second joint at an upper end of the other side thereof rotatable left and right about a center of a vertical axis of the first joint, a second link connected to the first link based on the second joint, rotatable left and right about a vertical axis of the second joint, and tiltable up and down about a horizontal axis of the second joint, a first mechanical mechanism provided to the first link and configured to simultaneously fix rotational motions of the first link and the second link or release at least one of the fixed first link and the second link for the rotational motion, and a head connection unit provided at one end of the second link and connected to an ultrasound head.

The first mechanical mechanism may simultaneously fix or release rotation of the first link and the second link by using a gear, a pulley, or a mechanism capable of generating frictional force.

The first mechanical mechanism may include a first lever, a worm gear configure to rotate in a horizontal direction by rotation of the first lever, a first worm and a second worm connected to both sides relative to the worm gear and configured to rotate in a vertical direction by the rotation of the worm gear in the horizontal direction, a first shaft and a second shaft connected to the respective worm wheels and each configured to rotate in the same direction as the connected worm wheel by the rotation of the worm wheel, a first tightener and a second tightener configured to tighten or loosen the respective shaft holders by the rotation of the respective shafts, and a first rotation axis and a second rotation axis respectively inserted into holes of the respective shaft holders, fixed to the respective joints, and configured to be simultaneously fixed or released by fastening or loosening the respective shaft holders.

The positioning arm apparatus may further include a second mechanical mechanism provided to the second link and configured to fix or release a tilting motion of the second link.

The second mechanical mechanism may include a second lever, a third shaft holder configured to be tightened or loosened by a screw of the second lever when the second lever rotates, and a third rotation axis inserted into a hole of the third shaft holder and configured to be fixed or released by tightening or loosening the third shaft holder.

The second mechanical mechanism may include a second lever provided with a screw that moves upward or downward when rotating, a third shaft holder configured to come in contact with the screw when the second lever moves downward by the rotation of the second lever and configured to lose its contact with the screw when the second lever moves upward, and a third rotation axis inserted into a hole of the third shaft holder and configured to be fixed or released by being in contact or losing contact with the third shaft holder.

Other features and aspects will be apparent from the following detailed description, the drawings, and the claims.

Figure 1:
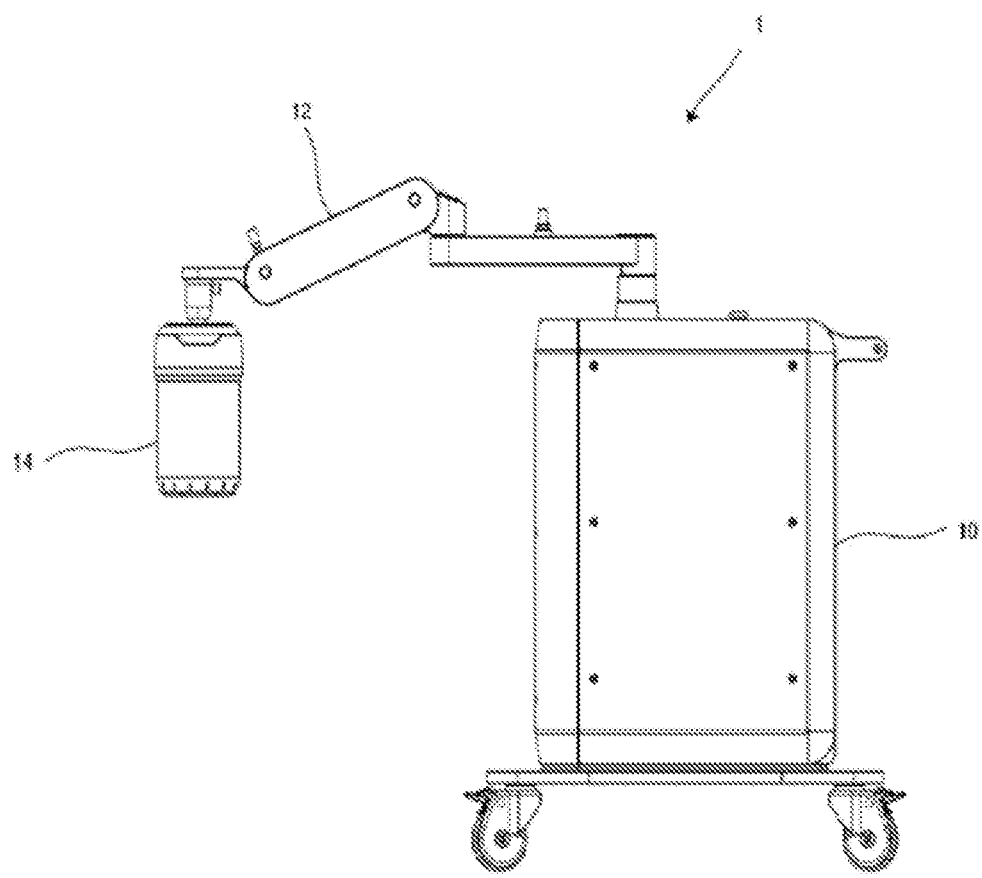
FIG. 1 is a view illustrating a configuration of an ultrasound system according to an embodiment of the present invention.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The advantages and features of the present invention and the manner of achieving the advantages and features will become apparent with reference to embodiments described in detail below together with the accompanying drawings. However, the present invention may be implemented in many different forms and should not be construed as being limited to the embodiments set forth herein, and the embodiments are provided such that this disclosure will be thorough and complete and will fully convey the scope of the present invention to those skilled in the art, and the present invention is defined only by the scope of the appended claims. The same reference numerals refer to the same components throughout this disclosure.

In the following description of the embodiments of the present invention, if a detailed description of related known functions or configurations is determined to unnecessarily obscure the gist of the present invention, the detailed description thereof will be omitted herein. The terms described below are defined in consideration of the functions in the embodiments of the present invention, and these terms may be varied according to the intent or custom of a user or an operator. Therefore, the definitions of the terms used herein should follow contexts disclosed herein.

It will be understood that each block of the flowchart illustrations, and combinations of blocks in the flowchart illustrations, can be implemented by computer program instructions (execution engine). These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer usable or computer-readable memory that can direct a computer or other programmable data processing apparatus to function in a particular manner, such that the instructions stored in the computer usable or computer-readable memory produce an article of manufacture including instruction means that implement the function specified in each block of block diagrams or in each step of the flowchart illustrations.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in each block of the block diagram or in each step of the flowchart illustrations.

Further, each block or each step of the flowchart illustrations may represent a module, segment, or portion of code, which includes one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Hereinafter, embodiments of the present invention will be described in detail with reference to the accompanying drawings. However, the present invention may be realized in various forms, and the scope of the present invention is not limited to such embodiments. The embodiments of the present invention are provided to aid those skilled in the art in the explanation and the understanding of the present invention.

FIG. 1 is a view illustrating a configuration of an ultrasound system according to an embodiment of the present invention.

Referring to FIG. 1, an ultrasound medical apparatus 1 according to an embodiment includes a body 10, a positioning arm apparatus 12, and an ultrasound head 14.

The positioning arm apparatus 12 is connected to an upper end of the body 10. A control unit configured to process a signal obtained from the ultrasound head 14, a driving unit configured to manipulate the positioning arm apparatus 12 may be mounted in the body 10.

The positioning arm apparatus 12 has an arm structure as a support structure for supporting the ultrasound head 14. The positioning arm apparatus 12 allows a user to move quickly and easily the ultrasound head 14 in various directions, such as horizontally and vertically, by a user operation so that the ultrasound head 14 can be moved to a position suitable for treating a treatment site.

The ultrasound head 14 includes a transducer. The transducer may include an imaging transducer and a treatment transducer, and may have a structure in which the imaging transducer and the treatment transducer are physically aligned in position with each other and assembled to each other.

The treatment transducer is configured to emit focused ultrasound for treating a patient. The treatment transducer generates a focused ultrasound (FUS) signal and focuses the focused ultrasound signal to the treatment site. The treatment transducer may have an array structure composed of a plurality of treatment transducers and the plurality of treatment transducers constituting the array may be arranged in a random form.

The imaging transducer is provided to obtain a diagnostic image of an object. An operator may perform FUS treatment using the treatment transducer while checking the diagnostic image obtained by the imaging transducer. The imaging transducer may be configured to transmit an ultrasound signal to the object and receive an ultrasound signal reflected from the object. For example, the imaging transducer may be configured to have a piezoelectric element or the like embedded in a cylindrical-shaped casing. An ultrasound wave may be transmitted and received through a bottom surface of the imaging transducer. The imaging transducer may be inserted through the center of a focused ultrasound-emitting surface of the treatment transducer. To this end, an insertion hole through which the imaging transducer is inserted may be formed at the center of the focused ultrasound-emitting surface of the treatment transducer.

An ultrasound diagnostic image of the object may be displayed on a screen of a display device. The display device may display a graphic user interface screen for performing an operation of the ultrasound system 1, a graphic user interface screen for receiving a user operation, a graphic user interface screen for displaying a progress result, and the like.

Figure 2:
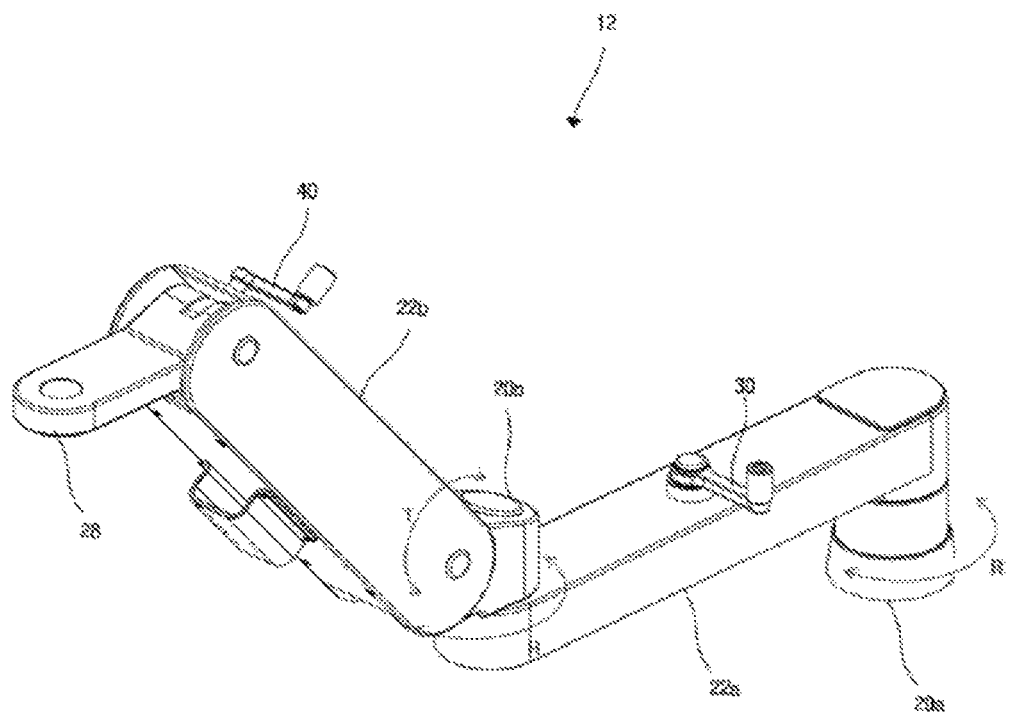
FIG. 2 is a view illustrating a configuration of a positioning arm apparatus according to an embodiment of the present invention.

FIG. 2 is a view illustrating a configuration of a positioning arm apparatus according to an embodiment of the present invention.

In FIG. 2, R denotes the direction of rotation (to left and right) and T denotes the direction of tilting (up and down). FIG. 2 illustrates a state in which the ultrasound head 14 of FIG. 1 is not attached to the positioning arm apparatus 12.

Referring to FIGS. 1 and 2, the positioning arm apparatus 12 includes a first link 22a, a second link 22b, a first mechanical mechanism 24 (in FIG. 3), a second mechanical mechanism 26 (in FIG. 3), and a head connection unit 28.

The first link 22a is provided with a first joint 20a at a lower end of one side and a second joint 20b at an upper end of the other side rotatable left and right about a vertical axis of the first joint 20a.

The second link 22b may be connected to the first link 22a based on the second joint 20b, rotatable left and right about a vertical axis of the second joint 20b, and tiltable up and down about a horizontal axis of the second joint 20b.

The positioning arm apparatus 12 according to an embodiment can perform a rotational motion at two positions and a tilting motion at one position. For example, the first link 22a and the second link 22b can perform a rotational motion and the second link 22b may perform a tilting motion. The ultrasound head may be moved without change in height of the ultrasound head through rotation at two positions and tilting at one position by a user operation.

In this case, the rotational motions of the first link 22a and the second link 22b may be simultaneously performed by means of a worm structure, a gear structure, and a link structure of the present invention. They can be operated with a small force using the worm structure.

The first mechanical mechanism 24 (in FIG. 3) is provided to the first link 22a and simultaneously fixes the first link 22a and the second link 22b in place or releases at least one of the first link 22a or the second link 22b so as to rotate it. When the first link 22a and the second link 22b are fixed, they are locked and cannot be rotated by a user operation below a preset force, and when the fixed links are released, they can be rotated without restrictions by a user operation. When the ultrasound head reaches at an intended position by rotating at least one of the first link 22a or the second link 22b by the user operation, the first link 22a and the second link 22b may be simultaneously fixed by the first mechanical mechanism 24 (in FIG. 3). The first mechanical mechanism 24 (in FIG. 3) may simultaneously fix and prevent rotation of the first link and the second link by using a gear, a pulley, or a mechanism capable of generating frictional force. The frictional force increases force for suppressing rotation of the first link and the second link.

The second mechanical mechanism 26 is provided to the second link 22b and fixes or releases an up-and-down tilting motion of the second link 22b. In this case, when the second link 22b is fixed, it cannot be tilted by a user operation, and when the fixed link 22b is released, the second link 22b can be titled by a user operation. When the ultrasound head is moved to an intended position after the second link 22b is tilted by the user operation, the second link 22b may be fixed by a fixing operation of the second mechanical mechanism 26.

The head connection unit 28 is provided at one end of the second link 22b and connected to the ultrasound head 14.

Figure 3:
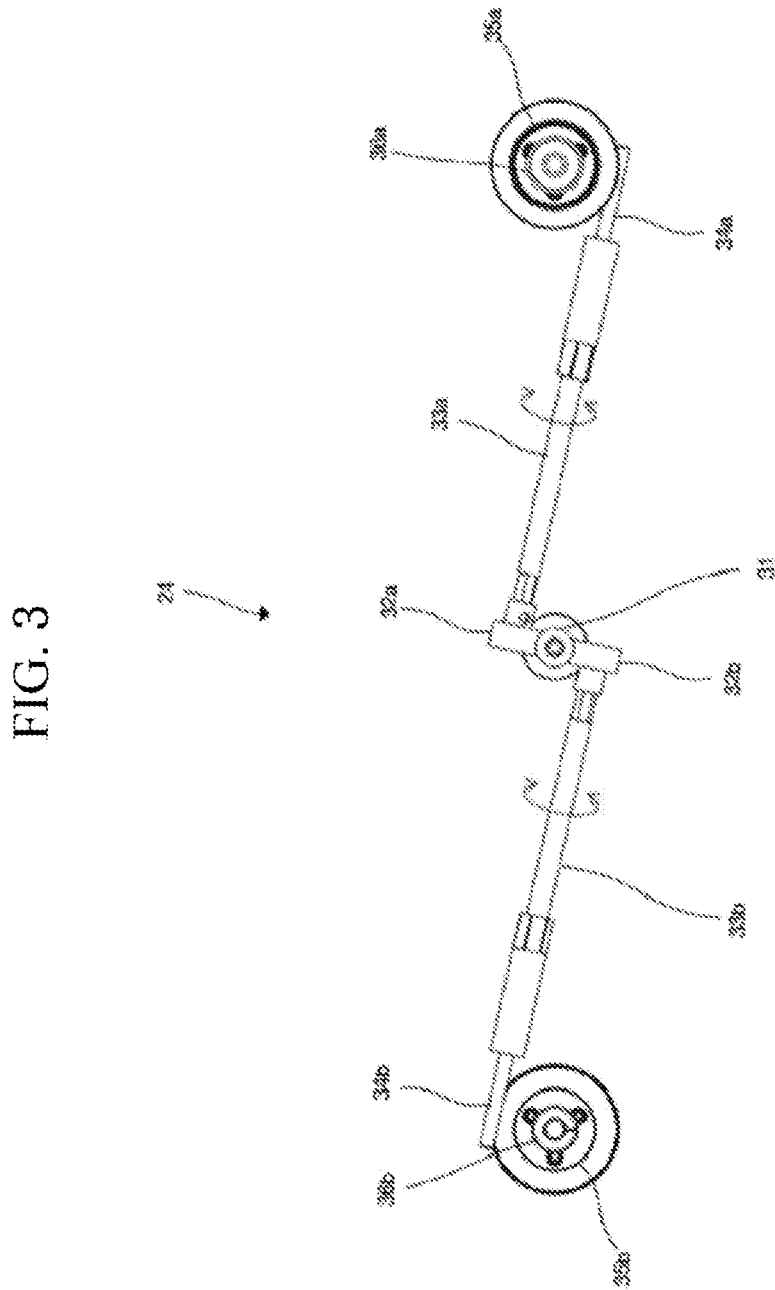
FIG. 3 is a view illustrating a configuration of a first mechanical mechanism according to an embodiment of the present invention.

FIG. 3 is a view illustrating a configuration of a first mechanical mechanism according to an embodiment of the present invention.

Referring to FIGS. 2 and 3, the first mechanical mechanism 24 includes a first lever 30, a worm gear 31, a first worm wheel 32a, a second worm wheel 32b, a first shaft 33a, a second shaft 33b, a first tightener 34a, a second tightener 34b, a first rotation axis 35a, and a second rotation axis 35b. The first lever 30 may be located outside the first link 22a, and the worm gear 31, the first worm wheel 32a, the second worm wheel 32b, the first shaft 33a, the second shaft 33b, the first tightener 34a, the second tightener 34b, the first rotation axis 35a, and the second rotation axis 35b may be located inside the first link 22a. The first worm wheel 32a, the first shaft 33a, the first tightener 34a, and the first rotation axis 35a may be positioned on the right side of the first mechanical mechanism 24 and provided for the rotational motion of the first link 22a. The first link 22a may rotate about the first rotation axis 35a by a user operation. In contrast, the second worm wheel 32b, the second shaft 33b, the second tightener 34b, and the second rotation axis 35b may be positioned on the left side of the first mechanical mechanism 24 and provided for the rotational motion of the second link 22b. The second link 22b may rotate about the second rotation axis 35b by a user operation.

The first lever 30 is provided outside the first link 22a and rotated by a user operation. When the user turns the first lever 30 in a predetermined direction (e.g., clockwise direction), the first link 22a and the second link 22b may be simultaneously fixed. When the user turns the first lever 30 in a reverse direction (e.g., counterclockwise direction), the fixed first link 22a and the fixed second link 22b may be simultaneously released. FIG. 3 illustrates the form of the first lever 30, but the first lever 30 is replaceable with a switch configured to apply an electrical signal.

The worm gear 31 is located between the first worm wheel 32a and the second worm wheel 32b, and is connected to the first lever 30 to rotate in a horizontal direction by rotation of the first lever 30.

The first worm wheel 32a and the second worm wheel 32b are connected to both sides relative to the worm gear 31, and rotate in the vertical direction by the rotation of the worm gear in the horizontal direction.

The first shaft 33a is connected to the first worm wheel 32a, the second shaft 33b is connected to the second worm wheel 32b, and the first shaft 33a is connected to the first worm wheel 32a, such that the first shaft 33a rotates in the same direction as the first worm wheel 32a by the rotation of the first worm wheel 32a and the second shaft 33b rotates in the same direction as the second worm wheel 32b by the rotation of the second worm wheel 32b.

The first tightener 34a tightens or loosens a first shaft holder 35a by the rotation of the first shaft 33a. Likewise, the second tightener 34b tightens or loosens a second shaft holder 35b by the rotation of the second shaft 33b.

The first rotation axis 35a is inserted into a hole of the first shaft holder 35a and fixed to the first joint 20a such that it is fixed or released by tightening or loosening the first shaft holder 35a. Likewise, the second rotation axis 35b is inserted into a hole of the second shaft holder 35b and fixed to the second joint 20b such that it is fixed or released by tightening or loosening the second shaft holder 35b. In this case, when the first rotation axis 35a and the second rotation axis 35b are simultaneously fixed, the first link 22a and the second link 22b cannot be moved by a user operation.

A process of simultaneously fixing the first link 22a and the second link 22b will be described herein below based on the structure described above. When the first lever 30 rotates in a predetermined direction (e.g., clockwise direction) by a user operation, the worm gear 31 connected to the first lever 30 is rotated in the same direction as the first lever 30, the first worm wheel 32a and the second worm wheel 32b that are connected to the worm gear 31 rotate in a direction perpendicular to the worm gear 31, the shafts 33a and 33b connected to the first worm wheel 32a and the second worm wheel 32b rotate in the same direction as the first worm wheel 32a and the second worm wheel 32b, each of the tighteners 34a and 34b is operated by the rotation of each of the shafts 33a and 33b, each of the shaft holders 35a and 35b is tightened by the operation of each of the tighteners 34a and 34b, and the rotation axises 36a and 36b inserted into the respective shaft holders 35*a* and 35*b* are simultaneously fixed by tightening the respective shaft holders 35*a* and 35*b*.

Figure 4:
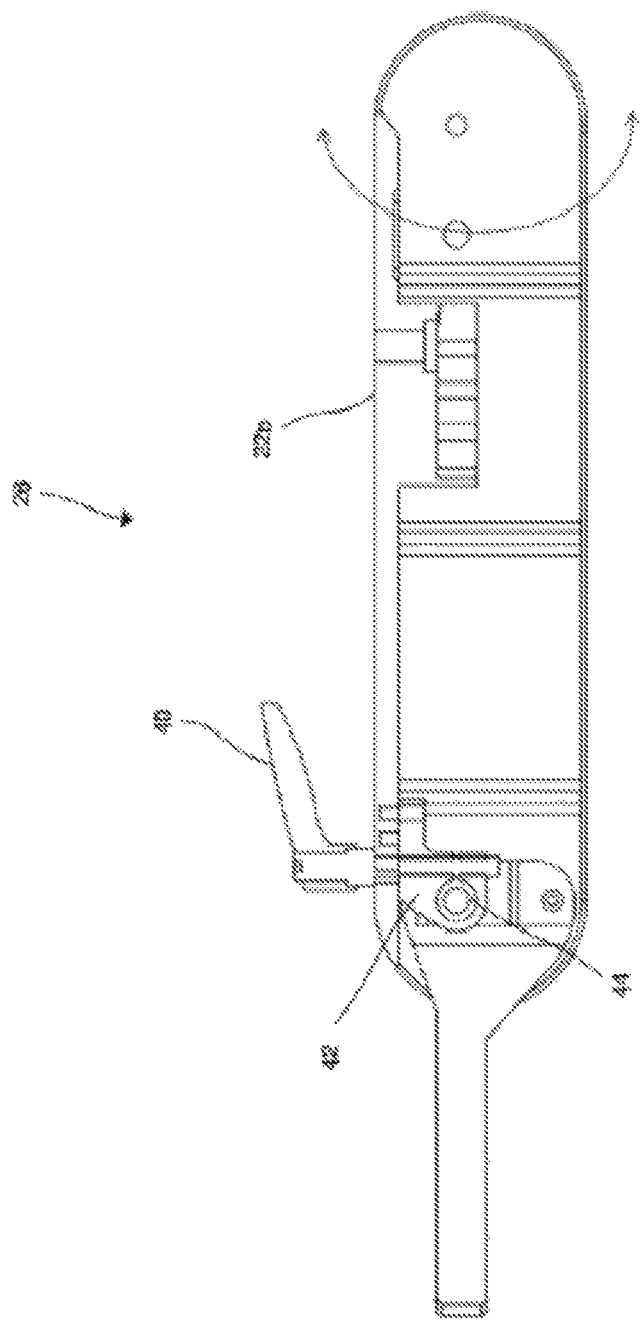
FIG. 4 is a view illustrating a configuration of a second mechanical mechanism according to an embodiment of the present invention.

FIG. 4 is a view illustrating a configuration of a second mechanical mechanism according to an embodiment of the present invention.

Referring to FIGS. 2 and 4, the second mechanical mechanism 26 includes a second lever 40, a third shaft holder 42, and a third rotation axis 44.

The second lever 40 has a structure that serves as a user's handle, located outside the second link 22*b*, and at least a portion of a screw thereof is provided inside the second link 22*b*.

The third shaft holder 42 is tightened or loosened by the screw of the second lever 40 when the second lever 40 rotates.

The third rotation axis 44 is inserted into a hole of the third shaft holder 42 and fixed or released by tightening or loosening the third shaft holder 42. The third shaft holder 42 surrounds the third rotation axis 44.

A process of fixing the tilting of the second link 22*b* will be described herein below based on the structure described above. When the second lever 40 rotates in a predetermined direction (e.g., clockwise direction) by a user operation, a screw portion of the second lever 40 rotates, and the third shaft holder 42 is tightened by the rotating screw. As a gap portion of the third shaft holder 42 is narrowed by tightening the third shaft holder 42, the third rotation axis 44 inserted into the hole of the third shaft holder 42 is tightened, and the third rotation axis 44 is fixed by frictional force between the third shaft holder 42 and the third rotation axis 44. When the third rotation axis 44 is fixed, the second link 22 cannot be tilted.

Figure 5:
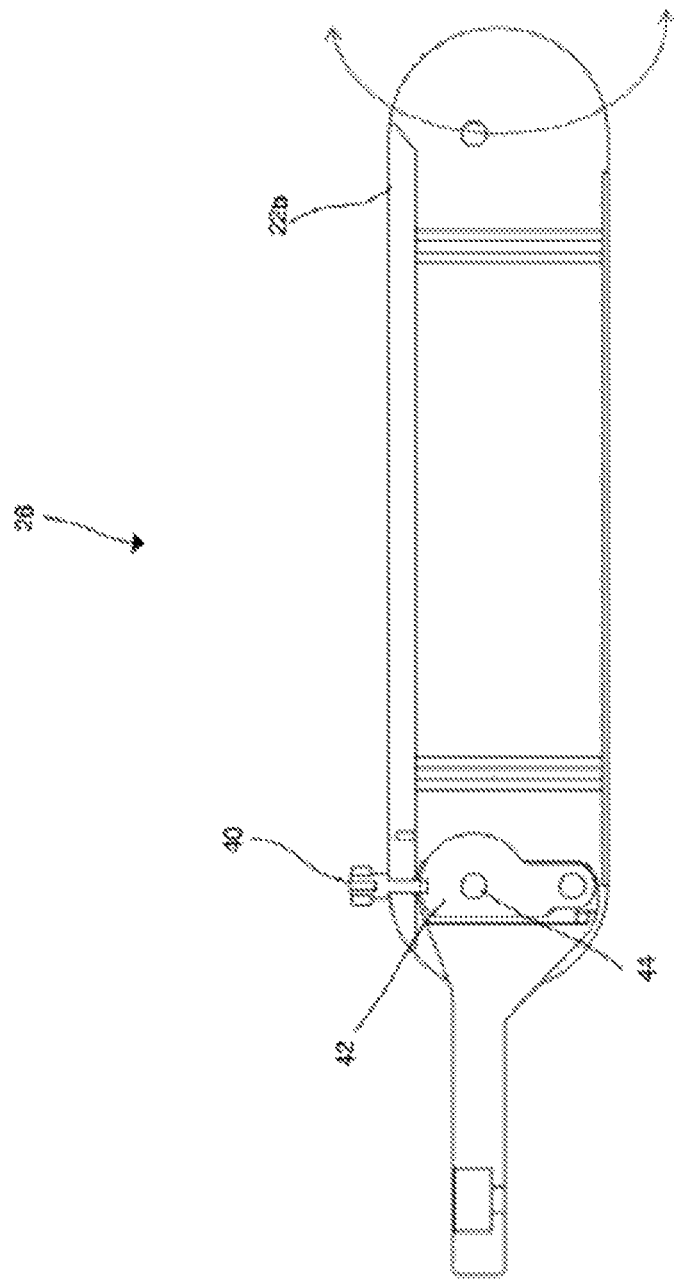
FIG. 5 is a view illustrating a configuration of a second mechanical mechanism according to another embodiment of the present invention.

FIG. 5 is a view illustrating a configuration of a second mechanical mechanism according to another embodiment of the present invention.

Referring to FIGS. 2 and 5, the second mechanical mechanism 26 includes a second lever 40, a third shaft holder 42, and a third rotation axis 44.

The second lever 40 serves as a user's handle and has a screw structure that simultaneously rotates located outside the second link 22*b*.

The third shaft holder 42 is pressed or released by the screw of the second lever 40 when the second lever 40 rotates.

The third rotation axis 44 is inserted into a hole of the third shaft holder 42 and fixed or released by pressing or releasing the third shaft holder 42. The third shaft holder 42 surrounds the third rotation axis 44.

A process of fixing the tilting of the second link 22*b* will be described herein below based on the structure described above. When the second lever 40 rotates in a predetermined direction (e.g., clockwise direction) by a user operation, the second lever 40 moves downward as a screw portion of the second lever 40 rotates. The third shaft holder 42 is pressed by the screw, the third rotation axis 44 inserted into the hole of the third shaft holder 42 is tightened by pressing the third shaft holder 42, and the third rotation axis 44 is fixed by frictional force between the third shaft holder 42 and the third rotation axis 44. When the third rotation axis 44 is fixed, the second link 22 cannot be tilted.

The positioning arm apparatus for an ultrasound head according to an embodiment can constantly move the ultrasound head without change in height of the ultrasound head according to a moving distance by rotation at two positions and tilting at one position.

Also, the positioning arm apparatus according to an embodiment can simultaneously fix or release rotational motion at two positions, and can be operated with a small force using a worm mechanism.

Further, the positioning apparatus according to an embodiment is operated only with a mechanical mechanism and thus can be miniaturized and lightweight. For example, conventionally, an electronic device (solenoid or motor) is used to fix an ultrasound head. A strong fixing force is required to securely fix the ultrasound head, which leads to the enlargement of the electronic device (solenoid or motor). This leads to an increase in size and weight of an apparatus, eventually resulting in a stationary apparatus, rather than a mobile apparatus. The positioning arm apparatus according to an embodiment uses purely mechanical parts, excluding the conventional electronic device, and thus can achieve a simplified, miniaturized, and lightweight structure.

Further, the positioning arm apparatus according to an embodiment may provide strong fixing force and easy maneuverability.

Heretofore, the present invention has been described by focusing on the exemplary embodiments. It can be understood by those skilled in the art to which the present invention pertains that the present invention can be implemented in modified forms without departing from the essential feature of the present invention. Therefore, the disclosed embodiments should be considered as illustrative rather than determinative. The scope of the present invention is defined by the appended claims rather than by the foregoing description, and all differences within the scope of equivalents thereof should be construed as being included in the present invention.

What is claimed is:

1. A positioning arm apparatus for an ultrasound head, the positioning arm apparatus comprising:
   a first link provided with a first joint at a lower end of one side thereof and a second joint at an upper end of the other side thereof rotatable left and right about a center of a vertical axis of the first joint;
   a second link connected to the first link based on the second joint, rotatable left and right about a vertical axis of the second joint, and tiltable up and down about a horizontal axis of the second joint;
   a first mechanical mechanism provided to the first link and configured to simultaneously fix rotational motions of the first link and the second link or release at least one of the fixed first link and the second link for the rotational motion;
   a second mechanical mechanism provided to the second link and configured to fix or release a tilting motion of the second link; and
   a head connection unit provided at one end of the second link and connected to an ultrasound head.

2. The positioning arm apparatus of claim 1, wherein the first mechanical mechanism is configured to simultaneously fix or release rotation of the first link and the second link by using a gear, a pulley, or a mechanism capable of generating frictional force.

3. The positioning arm apparatus of claim 2, wherein the first mechanical mechanism comprises:
   a first lever;
   a worm gear configure to rotate in a horizontal direction by rotation of the first lever;
   a first worm and a second worm connected to both sides relative to the worm gear and configured to rotate in a vertical direction by the rotation of the worm gear in the horizontal direction;

a first shaft and a second shaft connected to the respective worm wheels and each configured to rotate in the same direction as the connected worm wheel by the rotation of the worm wheel;

a first tightener and a second tightener configured to tighten or loosen the respective shaft holders by the rotation of the respective shafts; and a first rotation axis and a second rotation axis respectively inserted into holes of the respective shaft holders, fixed to the respective joints, and configured to be simultaneously fixed or released by fastening or loosening the respective shaft holders.

4. The positioning arm apparatus of claim 1, wherein the second mechanical mechanism comprises:

a second lever;

a third shaft holder configured to be tightened or loosened by a screw of the second lever when the second lever rotates; and a third rotation axis inserted into a hole of the third shaft holder and configured to be fixed or released by tightening or loosening the third shaft holder.

5. The positioning arm apparatus of claim 1, wherein the second mechanical mechanism comprises:

a second lever provided with a screw that moves upward or downward when rotating;

a third shaft holder configured to come in contact with the screw when the second lever moves downward by the rotation of the second lever and configured to lose its contact with the screw when the second lever moves upward; and a third rotation axis inserted into a hole of the third shaft holder and configured to be fixed or released by being in contact or losing contact with the third shaft holder.

* * * * *